United States Patent [19]

Bronstert et al.

[11] Patent Number: 4,599,433

[45] Date of Patent: Jul. 8, 1986

[54] REACTION OF OLEFINS WITH MALEIC ANHYDRIDE

[75] Inventors: Klaus Bronstert, Carlsberg; Hans-Henning Vogel, Frankenthal; Hans P. Rath, Gruenstadt, all of Fed. Rep. of Germany

[73] Assignee: BASF Aktiengesellschaft, Fed. Rep. of Germany

[21] Appl. No.: 717,109

[22] Filed: Mar. 28, 1985

[30] Foreign Application Priority Data

Mar. 29, 1984 [DE] Fed. Rep. of Germany ....... 3411531

[51] Int. Cl.$^4$ ............................................ C07D 307/60
[52] U.S. Cl. ................................................ 549/255
[58] Field of Search ......................................... 549/255

[56] References Cited

U.S. PATENT DOCUMENTS

| | | | |
|---|---|---|---|
| 2,297,039 | 9/1942 | van Melsen | 549/255 |
| 3,855,251 | 12/1974 | Cahill et al. | 549/255 |
| 3,935,249 | 1/1976 | Puskas et al. | 549/255 |
| 3,953,475 | 4/1976 | Puskas et al. | 549/255 |
| 4,278,604 | 7/1981 | Powell | 549/255 |
| 4,388,471 | 6/1983 | Wollenberg | 549/255 |

FOREIGN PATENT DOCUMENTS

| | | |
|---|---|---|
| 1480453 | 7/1977 | United Kingdom . |
| 2081274 | 2/1982 | United Kingdom . |

*Primary Examiner*—Henry R. Jiles
*Assistant Examiner*—Bernard I. Dentz
*Attorney, Agent, or Firm*—Keil & Weinkauf

[57] ABSTRACT

Olefinically unsaturated hydrocarbons, in particular dimeric or polymeric isobutene derivatives, which have a mean number average molecular weight $M_n$ of from 100 to 3000, are reacted with maleic anhydride in a molar ratio of maleic anhydride to olefin of from 0.2 to 3.0, in the presence of from 1 to 5000 ppm by weight of an alkoxide of titanium, of zirconium, of vanadium or of aluminum, at from 150° to 280° C., with formation of the corresponding succinic anhydride. These products are used for the preparation of anticorrosive agents or oil additives.

3 Claims, No Drawings

REACTION OF OLEFINS WITH MALEIC ANHYDRIDE

The present invention relates to a process for the reaction of an olefinically unsaturated hydrocarbon, in particular a dimeric or polymeric isobutene derivative, which has a mean number average molecular weight $M_n$ of from 100 to 3000, with maleic anhydride in a molar ratio of maleic anhydride to olefin of from 0.2 to 3.0, in the presence of from 1 to 5000 ppm by weight, based on the olefin, of an additive which prevents side reactions, at from 150° to 280° C., with formation of the corresponding succinic anhydride, and the use of these for the preparation of anticorrosive agents or oil additives.

Reactions of olefins with maleic anhydride at elevated temperatures give the corresponding adducts, for example the polyisobutylene-succinic anhydrides, in accordance with the following equation:

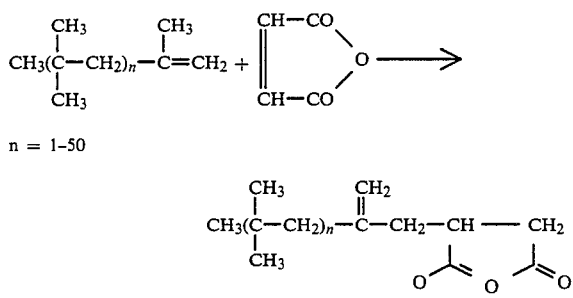

n = 1-50

However, reactions of this type at elevated temperatures require very long reaction times, for example 18 hours at 230° C. (cf. U.S. Pat. No. 306,901), so that acceleration of the addition reaction is desirable.

It is known that this requirement can be met by carrying out the reaction of olefinically unsaturated hydrocarbons with maleic anhydride in the presence of a catalytic amount of an additive. For example, in conventional processes, the reaction times are reduced to a satisfactory level by carrying out the addition reactions in the presence of small amounts, in general from 1 to 5000 ppm by weight, of substances such as furan derivatives (cf. U.S. Pat. No. 4,388,471), iodine (cf. GB-A-1 356 802), bromine (cf. GB-A-1 480 453), an α-bromodialkyl ketone (cf. U.S. Pat. Nos. 3,953,475 and 3,954,812), hydrogen chloride or calcium bromide (cf. U.S. Pat. No. 3,935,249), a hydantoin derivative (cf. U.S. Pat. No. 3,927,041), p-toluenesulfonic acid (cf. U.S. Pat. No. 3,855,251), a nickel salt (cf. GB-A-2 081 274) or a bromophenol (cf. U.S. Pat. No. 4,278,604).

In these conventional processes, however, the degree of conversion of the olefin is frequently low. Moreover, where halogen compounds are used, there is also considerable danger owing to the toxicity of the resulting reaction mixture and the decomposition of polyisobutylene at elevated temperatures. The conventional processes also have the disadvantage that brown or black solids are formed during the reaction and contaminate the kettle walls or, in more adverse cases, the reaction product. An even more disadvantageous feature is the formation of resin-like residues which render the product useless if it cannot be purified by distillation because of the molecular weight.

It is an object of the present invention to avoid the above disadvantages and to provide a process for the addition reaction of olefins with maleic anhydride in which the conversion is accelerated, the yield increased and the formation of resin by the maleic anhydride reduced.

We have found that this object is achieved, in accordance with the invention, if, in the process described at the outset, an alkoxide of titanium, of zirconium, of vanadium or of aluminum is used as the additive which prevents side reactions. $C_2$–$C_4$-alkoxides are preferably employed.

Suitable olefinically unsaturated hydrocarbons are all compounds which possess terminal double bonds or double bonds within a chain and have a mean molecular weight ($M_n$) of from 100 to 3000, and mixtures of these compounds.

For the purposes of the present invention, olefinically unsaturated hydrocarbons are, in particular, monomeric, oligomeric or polymeric $C_8$–$C_{14}$-alkenes whose chains may or may not be branched and which have a mean number average molecular weight $M_n$ of from 100 to 3000, determined from the osmotic pressure of the chloroform solution. The olefinically unsaturated hydrocarbons which can be subjected to the addition reaction include, for example, oct-1-ene, 2,4,4-trimethylpent-2-ene, 2-methyl-5-propylhex-1-ene, 3-cyclohexylbut-1-ene and the oligomers of $C_2$–$C_{20}$-olefins, for example the oligomers of ethylene, propylene, but-1-ene, isobutene, hex-1-ene, oct-1-ene, etc. and the polyisobutenes where $M_n$ is from 250 to 3000, and diisobutene. Preferred olefinically unsaturated hydrocarbons are dimeric or polymeric isobutene derivatives, ie. diisobutene, oligomeric isobutenes where $M_n$ is from 200 to 350, and polymeric isobutenes where $M_n$ is from 250 to 3000. Regarding the preparation of the oligomeric and polymeric isobutenes, reference may be made to the relevant literature (cf. for example H. Guterbock, Chemische Technologie der Kunststoffe, Polyisobutylen, SpringerVerlag, Berlin, Göttingen, Heidelberg 1959, or Ullmanns Encyklopädie der technischen Chemie, 4th edition, volume 19, 1980, pages 211–223, Verlag Chemie GmbH, D-6940, Weinheim).

In the reaction of the olefinically unsaturated hydrocarbons with maleic anhydride, the molar ratio of maleic anhydride to olefin, ie. the proportions of substances based on the number of moles of the components, is from 0.2 to 3.0, preferably from 0.5 to 2.0. A process in which equimolar amounts of olefin and maleic anhydride can be used is particularly preferred.

To avoid side reactions during the addition reaction of maleic anhydride, the reaction is carried out in the presence of from 1 to 5000, preferably from 5 to 1000, ppm by weight, based on the olefin used, of an additive which is intended to accelerate the desired addition reaction. As stated at the outset, additives of this type are known. They reduce the reaction time and increase the degree of conversion of the particular olefin. The principal side reactions are the formation of poly(maleic anhydride), which is obtained as a solid residue, or poly(maleic anhydride) with an olefinic component from free radical copolymerization of the olefin and the maleic anhydride, which is generally obtained in the form of a tacky resin.

The addition reaction with formation of the corresponding succinic anhydrides takes place at from 150° to 280° C., preferably from 180° to 230° C. The reaction itself can be carried out in a stirred autoclave, no solvent being required. The reaction times are usually not more than 20 hours. Advantageously, the reaction is carried out in the presence of an inert gas in such a manner that a pressure of from 5 to 1000, preferably from 5 to 100, mbar is established in the reaction vessel at the beginning of the reaction. Depending on the olefin component, the pressure in the reaction zone after heating to the reaction temperature is from 1 to 10 bar. A nitrogen or carbon dioxide atmosphere is preferably used as the inert atmosphere. When the reaction is complete, the autoclave is left to cool, and the reaction mass is preferably worked up by distillation. The reactants should as far as possible be anhydrous.

In the novel process, the additives used should be alkoxides, preferably the $C_2$–$C_4$-alkoxides, of titanium, of zirconium, of vanadium or of aluminum. Compounds of this type are known per se and are listed as Alfa products in, for example, the 1981 Alfa-Catalog of Ventrum GmbH, Zeppelinstrasse 7, D-7500 Karlsruhe 1. Particularly suitable alkoxides are titanium(IV) butoxide ($Ti(C_4H_9O)_4$), titanium(IV) isobutoxide ($Ti[(CH_3)_2CHCH_2O]_4$), titanium(IV) ethoxide ($Ti(C_2H_5O)_4$), titanium(IV) isopropoxide ($Ti(OC_3H_7)_4$), titanium(IV) n-propoxide ($Ti(C_3H_7O)_4$), zirconium n-butoxide/butanol complex (($C_4H_9O)_4Zr \cdot C_4H_9OH$), zirconium isopropoxide ($Zr(OC_3H_7) \cdot C_3H_7OH$), zirconium n-propoxide ($Zr(OC_3H_7)_4$), vanadium(V) tri-n-butoxide oxide ($VO(OC_4H_9)_3$), vanadium(V) triethoxide oxide ($VO(OC_2H_5)_3$), vanadium(V) tri-isopropoxide oxide of ($VO(OC_3H_7)_3$), vanadium(V) tris-n-propoxide oxide ($VO(OC_3H_7)_3$), aluminum isobutoxide ($Al(OC_4H_9)_3$), aluminum n-butoxide ($Al(OC_4H_9)_3$), aluminum-sec.-butoxide ($Al(OC_4H_9)_3$, aluminum tert.-butoxide ($Al(OC_4H_9)_3$), and aluminum isopropoxide ($Al(OC_3H_7)_3$). The stated alkoxides are in the liquid state, if appropriate as a complex with the corresponding alcohol, and are used in this form in the addition reaction. The purity of the compounds used is from 95 to 99% by weight, but from 90 to 99% by weight in the case of the aluminum alkoxides. The alkoxides used are soluble in the reaction mixture.

The particular advantages obtained using the invention are that the reaction of the olefinically unsaturated hydrocarbons with maleic anhydride is accelerated so that the reaction time is from 3.5 to 7.0, preferably from 3.5 to 5.0, hours, and the olefin is isomerized during the reaction, with the result that the yield is increased. At the same time, formation of resin from maleic anhydride or isomerization of this to fumaric acid is reduced. Another advantage is the absence of solvents and the fact that no toxic halogen-containing products are formed.

The resulting maleic anhydride/olefin products having mean molecular weights ($M_n$) of from 200 to 350 are used for the preparation of anticorrosive agents for aqueous or organic systems. The resulting olefin-succinic anhydrides having mean molecular weights ($M_n$) of from 250 to 3000 can be converted in a simple manner to compounds which are suitable as oil additives, eg. lubricant additives. For this purpose, they can be converted with polyhydric alcohols to the corresponding esters, or with amines to the corresponding salts, amines or imides, which are then mixed with, for example, lubricating oils (cf. GB-A-1 483 729 and GB-A-2 081 274). Processes of this type are known, and therefore require no further description here.

EXAMPLE 1

500 g of polyisobutene ($M_n$ 930), 50 g of maleic anhydride and 500 ppm of titanium(IV) n-butoxide [$Ti(C_4H_9O)_4$] are initially taken in a 1 l V2A stainless steel autoclave stirred with a magnetic stirrer, and the autoclave is flushed with nitrogen, brought to 2 mbar and then heated to 225° C. in an oil bath with vigorous stirring. After 4 hours at this temperature, the pressure in the reactor is let down and unreacted maleic anhydride (MA) is separated off by distillation under 2 mbar.

The reaction mixture which remains contains 40% by weight of unreacted polyisobutene (PIB) and 60% by weight of polyisobutenylsuccinic anhydride (PIBSA). Analysis is carried out by separation by preparative column chromatography using silica gel as adsorbent, hexane as an eluent for PIB, and a 9:1 (w/w) toluene-/acetone mixture as an eluent for PIBSA. The terminal double bond content of the unreacted PIB is 14%. The product is not found to contain any solid or resin-like residue. The only deposits found are on the stirrer and on the walls, and these deposits are dissolved in acetone after PIB and PIBSA have been removed by washing with toluene. The solution is transferred to a flask and evaporated down, and the residue is determined gravimetrically. It is found to amount to less than 0.2 g.

COMPARATIVE EXAMPLE 1

When the procedure is carried out exactly as described in Example 1 but without titanium(IV) n-butoxide, the conversion is found to be only 50% by weight, based on PIB, the terminal double bond content in the unreacted PIB is 14%, and a residue of 2.6 g is obtained. This also includes a solid residue, which is obtained by filtering the mixture under pressure, washing the filtration residue with toluene and then drying it.

EXAMPLE 2

An industrial mixture of 500 g 2,4,4-trimethylpent-1-ene and 2,4,4-trimethylpent-2-ene, and 500 ppm of titanium(IV) n-butoxide [$Ti(C_4H_9O)_4$], are initially taken in a 1 l V2A stainless steel autoclave stirred with a magnetic stirrer, and the autoclave is flushed with nitrogen, brought to 15 mbar and then heated to 225° C. in an oil bath. The addition of 350 g of MA at a rate of 100 g/h, and of an initial amount of 50 g, is effected by means of a metering pump. This addition is complete after 3 hours, and the mixture is allowed to continue reacting for a further 4 hours. After cooling, the mixture is filtered, and the residue is washed carefully with toluene and dried.

The reaction vessel, too, is flushed with toluene, the coating which remains is dissolved in acetone, and the solution is evaporated down in a flask. The total amount of residues from filtration and evaporation is less than 0.2 g. The olefin conversion is 70% by weight and is determined by distillation; the MA conversion is quantitative. The residual olefins contain 33% by weight of 2,4,4-trimethylpent-1-ene.

COMPARATIVE EXAMPLE 2

When the procedure is carried out exactly as described in Example 2, but without titanium(IV) n-butoxide, a similar conversion is achieved but 0.6 g of residue is obtained and the content of 2,4,4-trimethylpent-1-ene in the residual olefins is only 11%.

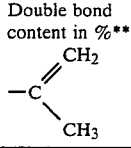

| | | | | | | Pressure [mbar] | | Temperature | Time | Conversion* | Residue | Double bond content in %** $-C\!\!\begin{array}{c}\nearrow CH_2 \\ \searrow CH_3\end{array}$ |
|---|---|---|---|---|---|---|---|---|---|---|---|---|
| Example | Type | Olefin | Amount [g] | MA [g] | Amount added [ppm] | 20° C. | 225° C. | [°C.] | [h] | [% by weight] | [g] | |
| 1 | PIB | ($M_n$ 930) | 500 | 50 | 500 | 2 | 500–1200 | 225 | 4 | 57 | <0.2 | 14 |
| Comparison 1 | PIB | ($M_n$ 930) | 500 | 50 | — | 2 | 500–1200 | 225 | 4 | 50 | 2.6 | 5 |
| 2 | 2,4,4-trimethyl-pentene | | 500 | 350 | 500 | 15 | 9–10 bar | 225 | 7 | 70 | 0.2 | 33 |
| Comparison 2 | 2,4,4-trimethyl-pentene | | 500 | 350 | — | 15 | 9–10 bar | 225 | 7 | 68 | 0.6 | 11 |

*based on olefin
**based on the total number of double bonds still present in the unreacted olefin

We claim:

1. A process for the reaction of an olefinically unsaturated hydrocarbon, which has a mean number average molecular weight $M_n$ of from 100 to 3000, with maleic anhydride in a molar ratio of maleic anhydride to olefin of from 0.2 to 3.0, in the presence of from 1 to 5000 ppm by weight, based on the olefin, of an additive which prevents side reactions, at from 150° to 280° C., with formation of the corresponding succinic anhydride wherein the additive used is an alkoxide of titanium, of zirconium, of vanadium or of aluminum.

2. A process as claimed in claim 1, wherein a $C_2$–$C_4$-alkoxide is used.

3. The process of claim 1, wherein the olefinically unsaturated hydrocarbon is a dimeric or polymeric isobutene derivative.

* * * * *